United States Patent
Roemisch et al.

(12)

(10) Patent No.: US 6,677,440 B1
(45) Date of Patent: *Jan. 13, 2004

(54) PROCESS FOR THE PREPARATION IN PURE FORM OF THE PROTEASE ACTIVATING BLOOD CLOTTING FACTOR VII, ITS PROENZYME OR A MIXTURE OF BOTH PROTEINS BY MEANS OF ION-EXCHANGE CHROMATOGRAPHY

(75) Inventors: Juergen Roemisch, Marburg (DE); Annette Feussner, Marburg (DE); Hans-Arnold Stoehr, Wetter (DE)

(73) Assignee: Aventis Behring GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/632,627

(22) Filed: Aug. 4, 2000

(30) Foreign Application Priority Data

Aug. 6, 1999 (DE) .......................... 199 37 219

(51) Int. Cl.[7] .................. A61K 38/00; A61K 35/14; C07K 1/14; C07K 1/16
(52) U.S. Cl. ................... 530/412; 530/380; 530/381; 530/415; 435/7.7; 424/94.1; 424/94.6
(58) Field of Search ................. 530/412, 413, 530/415, 416, 380; 435/7.7; 424/94.1, 94.6

(56) References Cited

FOREIGN PATENT DOCUMENTS

| DE | 199 26 531.3 | 6/1999 |
|---|---|---|
| DE | 199 03 693.4 | 10/1999 |
| EP | 0 952 215 | 10/1999 |

OTHER PUBLICATIONS

Choi–Miura, N., et al., *Purification and Characterization of a Novel Hyaluronan–Binding Protein (PHBP) from Human Plasma: It has Three EGF, a Kringle and a Serine Protease Domain, Similar to Hepatocyte Growth Factor Activator*, J. Biochem., vol. 119, pp. 1157–1165 (1996).

Derwent English Language Abstract for German Patent No. 199 03 693.4.

Nam–Ho Choi–Miura, et al. "Purification and Characterization of a Novel Hyaluronan–Binding Protein (PHBP) from Human Plasma: It Has Three EGF, a Kringle and a Serine Protease Domain, Similar to Hepatocyte Growth Factor Activator," J. Biochem, vol. 119, No. 6, pp. 1157–1165 (1996).

*Primary Examiner*—Karen Cochrane Carlson
*Assistant Examiner*—Samuel W. Lin
(74) *Attorney, Agent, or Firm*—Finnegan, Henderson, Farabow, Garrett and Dunner, L.L.P.

(57) ABSTRACT

A process for the preparation of a pure form of protein, wherein the protein is protease activating blood clotting factor VII, the proenzyme for the protease, or a mixture of both the-protease and the proenzyme, is described. The protein is obtained from biological fluids or through genetic engineering and is isolated by anion- and/or cation-exchange chromatography at a pH below the isoelectric point of the protein to be isolated, or by a combination of anion- or cation-exchange chromatography with a chromatography process and/or fractional precipitation at pH between 2.5 and 9.0.

17 Claims, No Drawings

SEQUENCE LISTING

```
<160> NUMBER OF SEQ ID NOS: 4

<210> SEQ ID NO 1
<211> LENGTH: 13
<212> TYPE: PRT
<213> ORGANISM: Unknown Organism
<220> FEATURE:
<223> OTHER INFORMATION: Description of Unknown Organism: Peptide
      characterizing the FVII-activity protease

<400> SEQUENCE: 1

Ile Tyr Gly Gly Phe Lys Ser Thr Ala Gly Lys His Pro
 1               5                  10

<210> SEQ ID NO 2
<211> LENGTH: 12
<212> TYPE: PRT
<213> ORGANISM: Unknown Organism
<220> FEATURE:
<223> OTHER INFORMATION: Description of Unknown Organism: Peptide
      characterizing the FVII-activity protease
<220> FEATURE:
<221> NAME/KEY: MOD_RES
<222> LOCATION: (9)
<223> OTHER INFORMATION: residue not identified

<400> SEQUENCE: 2

Leu Leu Glu Ser Leu Asp Pro Asp Xaa Thr Pro Asp
 1               5                  10

<210> SEQ ID NO 3
<211> LENGTH: 12
<212> TYPE: PRT
<213> ORGANISM: Unknown Organism
<220> FEATURE:
<223> OTHER INFORMATION: Description of Unknown Organism: Peptide
      characterizing the FVII-activity protease

<400> SEQUENCE: 3

Glu Phe His Glu Gln Ser Phe Arg Val Glu Lys Ile
 1               5                  10

<210> SEQ ID NO 4
<211> LENGTH: 12
<212> TYPE: PRT
<213> ORGANISM: Unknown Organism
<220> FEATURE:
<223> OTHER INFORMATION: Description of Unknown Organism: Peptide
      characterizing the FVII-activity protease
<220> FEATURE:
<221> NAME/KEY: MOD_RES
<222> LOCATION: (5)
<223> OTHER INFORMATION: residue not identified
<220> FEATURE:
<221> NAME/KEY: MOD_RES
<222> LOCATION: (7)
<223> OTHER INFORMATION: residue not identified
<220> FEATURE:
<221> NAME/KEY: MOD_RES
<222> LOCATION: (9)
<223> OTHER INFORMATION: residue not identified

<400> SEQUENCE: 4

Ser Lys Phe Thr Xaa Ala Xaa Pro Xaa Gln Phe Lys
 1               5                  10
```

PROCESS FOR THE PREPARATION IN PURE FORM OF THE PROTEASE ACTIVATING BLOOD CLOTTING FACTOR VII, ITS PROENZYME OR A MIXTURE OF BOTH PROTEINS BY MEANS OF ION-EXCHANGE CHROMATOGRAPHY

This application claims priority from German patent application No. 19937219.5 filed Aug. 6, 1999.

The invention relates to a process for the preparation in pure form of the protease activating blood clotting factor VII, its proenzyme or a mixture of both proteins, and of pharmaceutical preparations which contain the proteins mentioned individually or as a mixture.

German patent application 19 903 693.4 has already disclosed a protease for the activation of blood clotting factor VII, a process for its production, for its detection and for its inactivation, and pharmaceutical preparations which contain this protease. This protease, first isolated from plasma, occurs there together with a nonactivated form, which is designated below as "proenzyme". The protease activates blood clotting factor VII and accelerates clotting, as has been shown by numerous experiments. In the further investigation of the biological properties of this protein, identified as serine protease, it emerged that singlechain plasminogen activators, such as prourokinase, are also effectively activated. Moreover, inactivation of factors V and VIII in vitro was observed. In addition to the sequenced regions already described in German patent application 19 903 693.4, N-terminal sequencings of protease fractions were carried out. The following amino acid sequences characterize the FVII-activating prpotease: TYGGFKSTAGKHP (SEQ ID NO:1); LLESLDPDXTPD (SEQ ID NO:2); EFHEQSFRVEKI (SEQ ID NO:3); SKFTXAXPXQFK (SEQ ID NO:4); where X means not identified. The sequences of the protease mentioned elucidated up to now show that they agree 100% with sequences of the protease published by Choi-Miura (Choi-Miura et al. J. Biochem. 1996; 119: 1157 to 1165).

The investigations until now have especially concentrated on the protease in its activated form. The inactive form of the protease present in the plasma as a proenzyme was only recently discovered by means of a protein band pattern in the SDS-PAGE after reduction of the sample. Since, on the activation of the protease, cleavage and thus activation take place at a site of the primary structure typical for serine proteases two or more bands are visible on electrophoresis. On reduction of the chains which are connected by disulfide bridges, the individual bands become recognizable in accordance with their lower molecular weight, the proenzyme remaining as a large individual chain. This also became clear in more complex solutions after transfer of the proteins to membranes and subsequent Western blotting using suitable antibodies.

For therapeutic reasons, there is now an interest in having available both the protease in its activated form and the proenzyme, in addition to the mixture of the two proteins mentioned. Whereas the activated protease can be used for the rapid activation of blood clotting factor VII or the single-chain plasminogen activators in order to influence acute syndromes, the proenzyme form of the protease is especially to be chosen as a preferred agent for medium- to longer-term prophylaxis or treatment of inherited or acquired deficiency states or alternatively for increasing the plasma level beyond the physiological extent. However, it is to be taken into account here that the stabilization of an activated protease is difficult, since, for example, self-degradation can take place or the molecule can be unstable on account of its structural conditions. Previous studies have shown that the protease activating factor VII can be isolated and stabilized in its proenzyme form only under special circumstances.

The previous investigations have shown that the biological activities of this protease can be increased by calcium and/or heparin or substances related to the latter. This property has already been previously used in order to adsorb the protease on immobilized heparin and to obtain an enriched fraction. Moreover, it is already known that anion-exchange chromatography is also suitable for the purification of the protease. The combination of both purification steps is suitable for obtaining the protease in enriched form. An aprotinin matrix can also be used for the preparation in pure form of the activated protease.

A process for the preparation in pure form and simultaneous stabilization of the protease activating blood clotting factor VII and/or its proenzyme has now been found, in which they are obtained from biological fluids or those obtained in the case of preparation by genetic engineering by
 a) anion- and/or cation-exchange chromatography at a pH value below the isoelectric point of the protein to be isolated or
 b) a combination of anion- or cation-exchange chromatography with affinity chromatography
  and/or fractional precipitation at pH values between 2.5 and 9.0, preferably between 2.5 and 7.2, the affinity chromatography being carried out using calcium phosphate/hydroxyapatite
  a hydrophobic matrix,
  a chelate matrix,
  a matrix that is coated with an immobilized monoclonal or polyclonal antibody directed against the protein to be isolated, or its F(ab) or $F(ab)_2$ fragments.

A particularly suitable method for the preparation in pure form of the protease and/or its proenzyme is anion- and/or cation-exchange chromatography. The use of these methods for the preparation in pure form of the activated protease was admittedly proposed earlier, but the process conditions previously used did not produce completely satisfactory results. This is principally due to the fact that the risk of the activation of the proenzyme on contact with the surfaces of the matrices is very high. The object was therefore to develop a process which makes possible the preparation of the activated protease and of the proenzyme in a pure and stable form.

Surprisingly, it was then shown that very low pH values, in particular pH values between 2.5 and 7.2, damage neither the activated form of the protease nor the proenzyme and can therefore be employed to good effect in the adsorption and elution. By this means, almost trouble-free handling of the protease activating factor VII is made possible, since most other proteases circulating in the plasma are not active or only very slightly active in the acidic medium and the risk of proteolytic activation is thus minimized. The danger of the self-degradation of the protease is also decreased in this way. Since, as is known, extremely acidic pH values could include the risk of denaturation and thus bring about a loss in activity of the protease, the activity of the protease obtained from a strongly acidic medium occurring in the case of action on chromogenic substrates. It was shown in this case that both the protease and its proenzyme can be handled without loss of activity in the short term, up to a pH of 2.0. At a pH of 2.5 to approximately 7.2, the protease and its proenzyme can be stored for several months, the highest stabilities being observed at a pH of below 6.5.

In this case it was surprisingly found that anion- and/or cation-exchange chromatography at the low pH values mentioned can be used for the purification of the protease and of the proenzyme. This is so remarkable because in this case adsorption is possible on the exchanger matrices at pH values which lie below the isoelectric point of the protease or the proenzyme.

Up to now, there is still no scientific explanation of the interactions on which this adsorption is based. However, it is possible by means of this adsorption in the acidic medium to remove a large number of impurities that do not bind to the matrices at these pH values. A considerable enrichment of the protease on the matrix is thus achieved. After washing the matrix, the protease and/or the proenzyme can be eluted by an increase in the ionic strength.

For the preparation in pure form of the above mentioned proteins, the anion- and/or cation-exchange chromatography can be combined with chromatography and/or fractional precipitation. Independently of whether the above mentioned purification processes are employed individually or in any desired combination, it is recommended additionally to add protease inhibitors in all process steps, in order to block cleavage of the proenzyme into the activated protease. Suitable protein stabilizers that are added in this case are

- solubilizers, preferably hydroxyproline,
- detergents, preferably a polyoxyethylenesorbitan fatty acid ester (Tween®) or an octylphenoxypolyoxyethanol (Triton®),
- proteins, preferably albumin, gelatin, fibronectin and vitronectin or similar proteins,
- reductants, preferably dithiothreitol, mercaptoethanol or cysteine, and/or
- proteinase inhibitors such as aprotinin, $\alpha_2$-antiplasmin, C1-esterase inhibitor, inter-$\alpha$-trypsin inhibitor, antithrombin III/heparin or synthetic inhibitors.

A particularly good stabilization can be achieved during the preparation in pure form of the protease and of the proenzyme if, as further protein stabilizers,

- complexing agents of divalent ions, preferably ethylenediaminetetraacetic acid (EDTA), [ethylenebis (oxyethylenenitrilo)]tetraacetic acid (EGTA), or citrate and/or
- divalent ions, preferably calcium ions, and/or
- amino acids, preferably glutamate, arginine, lysine or glycine, and/or
- sugars, preferably glucose, arabinose, mannose or mannitol, and/or
- alcohols, preferably ethylene glycol or polyethylene glycol, are added.

The abovementioned process steps can also additionally be combined with fractional precipitation of the protease and/or its proenzyme from its solution, which is carried out by addition of

- polyethylene glycol from a concentration of at least 10% by weight or
- ammonium sulfate from a concentration of at least 15% by weight.

It is particularly worthy of note that in the processes described above the proenzyme form of the protease can also be obtained in pure form. As a matter of fact, it was seen that ion-exchange chromatography, under the said acidic conditions, using a solution which especially contained the proenzyme, led to an eluate which contained the proenzyme exclusively or at least to a very greatly enriched extent. In this case, the nativity of the proenzyme thus obtained can be determined with the aid of one of the activity tests which are described in German patent application 196 26 531.3. i.e., for example, by the photometric determination of the extinction occurring on action on chromogenic substrates or by the single-chain formation occurring after reduction of the sample, which can be detected by SDS-PAGE/Western blotting. This shows that according to the invention the preparation of the proenzyme is possible in a rapid and efficient manner and with a high yield.

When using the abovementioned process steps, it is thus possible to obtain both the purified protease activating factor VII, its proenzyme or alternatively a mixture of the activated protease and the proenzyme. A route which is particularly worthy of recommendation for the preparation of a pure activated protease consists in the chromatographic separation of the protease activating factor VII from its proenzyme by means of stepwise elution, in which a substance is immobilized on the support material which has bonds of different strength to the protease on the one hand and to the proenzyme on the other hand. Different eluates can thus be obtained which contain either only the activated protease or only the proenzyme.

To obtain the proenzyme, an inhibitor with strong affinity for the activated protease is in this case immobilized on the matrix. Serine protease inhibitors, in particular C1 esterase inhibitor, $\alpha_2$-antiplasmin, antithrombin III (with admixture of heparin to the application solution) or low molecular weight, high affinity inhibitors, which can also be of synthetic nature, are especially suitable for this. The proenzyme which is not bound or less firmly bound to the matrix is then found in the solution flowing through the column. On the other hand, for the preparation in pure form of the activated protease, an inhibitor is immobilized on the matrix which only has a weak inhibitory potential and reversibly binds the activated protease. In this case, after washing off the proenzyme, the active protease bound to the matrix is eluted and can thus be obtained in pure form. A suitable support material for this process variant is, for example, one treated with aprotinin or low molecular weight, reversible inhibitors, which can also be of synthetic nature.

Of course, antibodies or fragments thereof, which can differ between the activated protease and the proenzyme, can also be used for the preparation of the said proteins in pure form. For this, monoclonal antibodies can especially be employed which can recognize "neoepitopes" after activation of the protease, i.e., for example, the activation or cleavage site of the protein.

Under the affinity-chromatography processes to be employed according to the invention, adsorption on calcium phosphate/hydroxyapatite is to be emphasized as a simple and rapid method for the enrichment of the protease and/or of the proenzyme. In this case, the solution which contains the protease and the proenzyme is mixed with calcium phosphate at a pH of between 2.5 and 9.0, preferably between 2.5 and 7.2. After subsequent sedimentation, e.g. by centrifugation or by filtration, the sediment, if appropriate after resuspending one or more times in a buffer solution, is eluted with addition of, for example, 0.2 M sodium citrate. The protease and the proenzyme are then found in the eluate.

The adsorption of the protease on hydrophobic matrices or on hydrophobic ligands that are coupled to appropriate matrices can also be used according to the invention. Examples are phenyl- or octyl-sepharoses or a phenylalanine coupled to a matrix. The elution of the bound protein is carried out in a manner known per se using a buffered solution of low ionic strength, which can contain phenylalanine, glycerol or ethylene glycol.

Since the protease and the proenzyme enter into an interaction with cations, especially with calcium and magnesium ions, which is confirmed by an increase in their activity in the presence thereof, chromatography by means of so-called "chelate matrices" suggests itself for enrichment thereof from corresponding solutions. Chelate compounds with zinc, copper or nickel ions are particularly suitable in this case. After the washing of the matrix loaded with the protease, an imidazole buffer can also be employed for the elution of bound proteins, if appropriate with a linear gradient.

The process according to the invention can also contain an affinity-chromatography purification step in which the support material employed is a matrix on which monoclonal or polyclonal antibodies directed against the said proteins, or their F(ab) or their F(ab)$_2$ fragments or other substances suitable for the reversible binding of the said proteins, are immobilized.

The protease obtained by the process according to the invention, its proenzyme or a mixture of both proteins can be stored without loss of activity in the acidic pH range at pH values of approximately 2.5 to 7.2 with or without the addition of additional stabilizers, while in the alkaline range addition of stabilizers is necessary.

Therapeutically, the said activated protease, the proenzyme or the mixture of both compounds can be used to assist blood clotting in the case of a tendency to bleeding, in the case of absence of factors of the endogenous clotting branch or as FEIBA (=factor VIII bypassing activity), but also for the endogenous and exogenous activation of plasminogen activators such as prourokinase or single-chain tPA. This activity can also be employed in combination with single-chain or double-chain plasminogen activators or anticoagulants by use of the said protease for the prophylaxis or therapy of thromboembolic disorders. Syndromes which are associated with thrombotic complications, such as cardiac infarct, angina pectoris, stroke or leg vein thromboses, can thus be successfully treated.

A further subject of the invention is therefore a pharmaceutical preparation which contains an amount of the protease activating blood clotting factor VII and/or its proenzyme form sufficient for the dissolution of fibrin-containing thrombi. This preparation can also moreover contain single-chain plasminogen activators and/or anticoagulants. Expediently, a proteinase stabilizer or a reductant such as dithiothreitol, mercaptoethanol, or cysteine is additionally added to the preparation in order to reduce the risk of polymer formation during processing or on storage.

Fibrinolytic processes also play a part in wound-healing processes. In this case, the said protease and/or the proenzyme can be administered intravenously or locally, subcutaneously, intradermally, intramuscularly or, in the case of injuries and wounds, as a constituent of a fibrin adhesive or alternatively topically or bound to a suitable carrier matrix, e.g. in the form of a web or of a patch, where combination with growth factors can be expedient. In general, a pharmaceutical preparation of this type is used in liquid or lyophilized form, to which protein stabilizers known per se can be added, i.e., for example, complexing agents, divalent cations such as calcium, amino acids such as glutamate, arginine, lysine or glycine and/or sugars such as glucose, arabinose, mannose or mannitol.

Moreover, the protease and/or its proenzyme can also be employed for the coating of articles, consisting of plastics or metals, to be implanted in the body, such as synthetic heart valves, blood vessels, but also cannulas inserted for taking blood or for artificial feeding.

The invention is illustrated by the following examples:

EXAMPLE 1

Preparation in Pure Form by Means of Immobilized Monoclonal Antibodies

Monoclonal antibodies that are directed against the protease activating factor VII were coupled to BrCN-sepharose. 20 ml of this mAb matrix were packed into a column and the resin was equilibrated with 50 mM sodium citrate, 0.1 M sodium chloride (NaCl), 0.1 M arginine×HCl, pH 6.0.

100 ml of citrate plasma were pumped through the column and the matrix was then washed with 50 mM sodium citrate, 1 M NaCl, 0.1 M arginine×HCl, pH 6.0. The column was then washed again with the equilibration buffer, after which elution with 0.1 M glycine, pH 2.5, followed. The eluate (about 30 ml) was collected in a volume of 3 ml of a 200 mM sodium citrate solution, pH 5.5, with stirring and then adjusted to a pH of 4.5.

The eluate solution was used for further analysis. An SDS-PAGE with subsequent transfer to a PVDF membrane and detection of the factor VII activator band was carried out using the unreduced and using the reduced sample. Activity tests of the proteins thus obtained were carried out according to the process described in German patent application 199 26 531.3, namely the activation of prourokinase and factor VII, with subsequent detection of urokinase or activated factor VII. The amounts of protease tested in this system, determined as protease antigen, correspond to the expected theoretical activity, whereby the activity of the isolated protease or of the proenzyme with respect to the biological activity was shown.

EXAMPLE 2

Anion-exchange Chromatography

A solution containing the proenzyme form of the factor VII-activating protease which still contained contaminations by other proteins was pumped onto a Mono, Q Sepharose in a buffer solution of 20 mM Na acetate, 0.1 M glycine, pH 4.5 and then washed with the abovementioned buffer. The fraction passing through was collected. Bound proteins were eluted using 20 mM Na acetate, 2 M NaCl, pH 4.5. The eluate was diluted in a buffer of 5 mM Na citrate, 50 mM NaCl, pH 6.0, and investigated in the test systems mentioned in Example 1. Aliquots were stored at 4 to 8° C. or frozen at −20° C.

After storage of the eluate solution at 6° C. for several days, the tests were repeated, the dilutions of the (thawed) samples in each case being carried out shortly before the test.

SDS-PAGEs/Western blots confirmed that the protease had been isolated in its proenzyme form. After SDS-PAGE and staining of proteins by means of Coomassie Blue, in addition to the protease a number of contaminating proteins, which were also to be found in the fractions flowing through, were visible in the starting solution (before chromatography). The protease was represented as a band corresponding to the proenzyme form (i.e. even after reduction) in pure form. The activity tests (see Example 1) confirmed the nativity of the protein in the sense of the retainment of the biological activities.

What is claimed is:

1. A process for the preparation of a protein wherein the protein is the pure form of the protease activating blood clotting factor VII, the pure form of a proenzyme for the protease, or a mixture of both the pure form of the protease and the pure form of the proenzyme, and wherein the protein is obtained from biological fluids or through genetic engineering and is isolated by a combination of anion-exchange or cation-exchange chromatography with a chromatography separation process, or with a fractional precipitation, or with a combination of both a chromatography separation process and a fractional precipitation performed at a pH value between 2.5 and 9.0, wherein during said chromatography separation process the protein is absorbed on one of:
- a) calcium phosphate/hydroxyapatite
- b) a hydrophobic matrix;
- c) a chelate matrix;
- d) a matrix which is coated with an immobilized monoclonal or polyclonal antibody directed against the protein to be isolated, or F(ab) or F(ab)$_2$ fragments of antibodies directed against the protein to be isolated; or
- e) a matrix which comprises an immobilized inhibitor which has a weak or strong binding affinity for the protein.

2. The process according to claim 1, wherein the fractional precipitation of the protein from its solution is carried out by addition of:
- a) polyethylene glycol from a concentration of at least 10% by weight, or
- b) ammonium sulfate from a concentration of at least 15% by weight.

3. The process according to claim 1, wherein protease activating blood clotting factor VII is separated from its proenzyme by chromatography separation, wherein:
- a) a substance having bonds of different strength to the protease and proenzyme is immobilized on a support material;
- b) the proteins are eluted sequentially;
- c) the different eluates are collected separately from one another; and
- d) the respective protease or proenzyme is isolated from its eluate.

4. The process according to claim 1, wherein the immobilized inhibitor is used to obtain the proenzyme, wherein:
- a) the inhibitor has a strong affinity for the activated protease;
- b) the inhibitor is natural or synthetic; and
- c) the proenzyme which is not bound to the matrix is found in the solution flowing from the column.

5. The process according to claim 4, wherein the inhibitor is
- a) a serine protease inhibitor, such as C1 esterase inhibitor, $\alpha_2$-antiplasmin, antithrombin III/heparin; or
- b) a low molecular weight, high affinity inhibitor.

6. The process according to claim 1, wherein the immobilized inhibitor used to obtain the protease has a weak affinity for and reversibly binds the activated protease; wherein:
- a) the unbound proenzyme is washed off the matrix; and
- b) the active protease bound to the matrix is eluted and collected.

7. The process according to claim 6, wherein the inhibitor is aprotinin or a low molecular weight, reversible inhibitor, and wherein the inhibitor is natural or synthetic.

8. The process according to claim 1, wherein the protein is absorbed on calcium phosphate/hydroxyapatite, wherein:
- a) a solution which contains the protein is mixed with calcium phosphate at a pH of between 2.5 and 9.0;
- b) the protein is collected by sedimentation;
- c) the sediment is resuspended one or more times in a buffer solution;
- d) the protein is eluted; and
- e) the protein is found in the eluate.

9. The process according to claim 1, wherein the protein is absorbed on a hydrophobic matrix, wherein:

hydrophobic ligands are coupled to the hydrophobic matrix; and the absorbed protein is eluted in a buffered solution of low ionic strength.

10. The process according to claim 9, wherein the hydrophobic ligands are the phenyl derivative of aliphatic hydrophobic agarose beads, the octyl derivative of aliphatic hydrophobic agarose beads, or phenylalamine.

11. The process according to claim 1, wherein the protein is absorbed on a chelate matrix, wherein:
- a) the chelate matrix comprises chelate compounds which comprise zinc, copper, nickel ions, or a combination thereof; and
- b) after washing the matrix loaded with the protein, a buffer is used to elute the protein.

12. The process according to any one of claims 1–11, which is carried out in the presence of one or more protein stabilizers selected from:
- a) complexing agents of divalent ions;
- b) divalent ions;
- c) amino acids;
- d) sugars;
- e) solubilizers;
- f) detergents;
- g) alcohols;
- h) proteins;
- i) reductants; and
- j) protease inhibitors.

13. The process according to claim 12, which is carried out in the presence of one or more protein stabilizers wherein:
- a) the complexing agent of divalent ions is ethylenediaminetetraacetic acid, ethylenebis(oxyethylenenotrilo) tetraacetic acid, or citrate,
- b) the divalent ions are calcium ions;
- c) the amino acids are glutamate, arginine, lysine, or glysine;
- d) the sugar is glucose, arabinose, mannose, or mannitol;
- e) the solubilizer is hydroxyproline;
- f) the detergent is a polyoxyethylenesorbitan fatty acid ester or a octylphenoxypolyoxyethanol;
- g) the alcohol is ethylene glycol or polyethylene glycol;
- h) the protein is, albumin, gelatin, fibrobectin, vitronectin, or similar proteins;
- i) the reductant is dithiothreitol, mercaptoethanol, or cysteine; or
- j) the protease inhibitor is aprotinin, $\alpha_2$-antiplasmin, C1-estarase inhibitor, inter-$\alpha$-trypsin inhibitor or antithrombin III/heparin inhibitor.

14. A process for the preparation of a protein wherein the protein is the pure form of the protease activating blood clotting factor VII, the pure form of the proenzyme for the protease, or a mixture of both the pure form of the protease and the pure form of the proenzyme, and wherein the protein is obtained from biological fluids or through genetic engineering and is isolated by anion-exchange chromatography, cation-exchange chromatography, or a combination of both anion-exchange and cation-exchange chromatography processes at a pH below the isoelectric point of the protein to be isolated.

15. The process as claimed in claim 1, wherein the chromatography process, the fractional precipitation, or the combination of both a chromatography process and a fractional precipitation is performed at a pH value between 2.5 and 7.2.

16. The process according to claim 14, which is carried out in the presence of one or more protein stabilizers selected from:

a) complexing agents of divalent ions;

b) divalent ions;

c) amino acids;

d) sugars;

e) solubilizers;

f) detergents;

g) alcohols h) proteins;

i) reductants; and j) protease inhibitors.

17. The process according to claim 12, wherein the protease inhibitors are synthetic inhibitors.

* * * * *